United States Patent [19]
Kenyon

[11] Patent Number: 6,119,723
[45] Date of Patent: Sep. 19, 2000

[54] APPARATUS FOR VARYING THE FLOW AREA OF A CONDUIT

[75] Inventor: Barton John Kenyon, Erskineville, Australia

[73] Assignee: ResMed Limited,, North Ryde, Australia

[21] Appl. No.: 09/023,348

[22] Filed: Feb. 13, 1998

[30] Foreign Application Priority Data

Feb. 14, 1997 [AU] Australia .................................. PO5113

[51] Int. Cl.$^7$ ............................. F16K 15/00; F16K 31/08
[52] U.S. Cl. ......................... 137/527; 137/527.8; 251/65; 251/336
[58] Field of Search ................................. 137/527, 527.8; 251/65, 336; 73/861.76, 861.75, 861.74

[56] References Cited

U.S. PATENT DOCUMENTS

| | | |
|---|---|---|
| Re. 35,295 | 7/1996 | Estes et al. . |
| Re. 35,339 | 10/1996 | Rapoport . |
| 950,816 | 3/1910 | Eriksson et al. . |
| 3,099,985 | 8/1963 | Wilson et al. . |
| 3,191,596 | 6/1965 | Bird et al. . |
| 3,267,935 | 8/1966 | Andreasen et al. . |
| 3,362,404 | 1/1968 | Beasley . |
| 3,485,243 | 12/1969 | Bird et al. . |
| 3,669,108 | 6/1972 | Sundblom et al. . |
| 3,741,208 | 6/1973 | Jonsson et al. . |
| 3,783,893 | 1/1974 | Davison . |
| 3,802,417 | 4/1974 | Lang . |
| 3,834,383 | 9/1974 | Weigl et al. . |
| 3,840,006 | 10/1974 | Buck et al. . |
| 3,859,995 | 1/1975 | Colston . |
| 3,863,630 | 2/1975 | Cavallo . |
| 3,896,800 | 7/1975 | Cibulka . |
| 3,903,875 | 9/1975 | Hughes . |
| 3,914,994 | 10/1975 | Banner ..................................... 137/554 |
| 3,932,054 | 1/1976 | McKelvey . |
| 3,961,627 | 6/1976 | Ernst et al. . |
| 3,972,327 | 8/1976 | Ernst et al. . |
| 3,985,467 | 10/1976 | Lefferson . |
| 3,992,598 | 11/1976 | Welsh et al. . |
| 3,995,661 | 12/1976 | Van Fossen ................................ 251/65 |
| 4,006,634 | 2/1977 | Billette et al. . |
| 4,031,885 | 6/1977 | Davis et al. . |
| 4,036,221 | 7/1977 | Hillsman et al. . |
| 4,050,458 | 9/1977 | Friend . |
| 4,082,093 | 4/1978 | Fry et al. . |
| 4,083,245 | 4/1978 | Osborn . |
| 4,109,749 | 8/1978 | Sweet . |
| 4,207,884 | 6/1980 | Isaacson . |
| 4,231,365 | 11/1980 | Scarberry . |
| 4,239,039 | 12/1980 | Thompson . |
| 4,249,527 | 2/1981 | Ko et al. . |

(List continued on next page.)

FOREIGN PATENT DOCUMENTS

| | | |
|---|---|---|
| B-59270/90 | 12/1990 | Australia . |
| A-62221/90 | 3/1991 | Australia . |
| A-33877/93 | 4/1993 | Australia . |
| A-38508/93 | 7/1993 | Australia . |

(List continued on next page.)

OTHER PUBLICATIONS

New! Breas PV 100 CPAP First Class Quality and Function. At the right Price; Jul. 4, 1998, pp. 1–2.
PV 101 Bi Level CPAP and PV 102 Bi–Level Time; pp. 1–3.
Prodigy Medical Supplies Co. Ltd.; CPAP.
Puritan Bennett; Companion 318 Nasal CPAP System; May 1993.

(List continued on next page.)

Primary Examiner—Denis L. Ferensic
Assistant Examiner—Joanne Y. Kim
Attorney, Agent, or Firm—Holland & Hart LLP

[57] ABSTRACT

An apparatus (10) for varying the flow area of a conduit (12). The apparatus comprises a flap (14) mounted in said conduit (12) which is off-center pivotally mounted to pivot in response to flow of fluid (F) through said conduit (12). The apparatus (10) also includes biasing means associated with the flap to rotationally urge the flap against the action of the flow (F).

17 Claims, 5 Drawing Sheets

U.S. PATENT DOCUMENTS

| | | |
|---|---|---|
| 4,251,027 | 2/1981 | Dehart et al. . |
| 4,262,667 | 4/1981 | Grant . |
| 4,281,651 | 8/1981 | Cox . |
| 4,301,833 | 11/1981 | Donald, III .............................. 137/527 |
| 4,323,064 | 4/1982 | Hoenig et al. . |
| 4,387,722 | 6/1983 | Kearns . |
| 4,389,901 | 6/1983 | Lake . |
| 4,393,869 | 7/1983 | Boyarsky et al. . |
| 4,396,034 | 8/1983 | Cherniak ................................ 137/527 |
| 4,421,113 | 12/1983 | Gedeon et al. . |
| 4,430,995 | 2/1984 | Hilton . |
| 4,448,058 | 5/1984 | Jaffe et al. . |
| 4,449,525 | 5/1984 | White et al. . |
| 4,457,303 | 7/1984 | Durkan . |
| 4,499,914 | 2/1985 | Schebler . |
| 4,501,273 | 2/1985 | McGinnis . |
| 4,507,976 | 4/1985 | Banko . |
| 4,519,388 | 5/1985 | Schwanbom et al. . |
| 4,527,557 | 7/1985 | DeVries et al. . |
| 4,530,334 | 7/1985 | Pagdin ................................ 73/861.76 |
| 4,535,766 | 8/1985 | Baum . |
| 4,537,190 | 8/1985 | Caillot et al. . |
| 4,539,984 | 9/1985 | Kiszel et al. . |
| 4,552,141 | 11/1985 | Torri . |
| 4,558,710 | 12/1985 | Eichler . |
| 4,559,940 | 12/1985 | McGinnis . |
| 4,567,888 | 2/1986 | Robert et al. . |
| 4,579,114 | 4/1986 | Gray et al. . |
| 4,579,115 | 4/1986 | Wallroth et al. . |
| 4,584,996 | 4/1986 | Blum . |
| 4,592,349 | 6/1986 | Bird . |
| 4,612,928 | 9/1986 | Tiep et al. . |
| 4,635,631 | 1/1987 | Izumi . |
| 4,637,385 | 1/1987 | Rusx . |
| 4,637,386 | 1/1987 | Baum . |
| 4,649,755 | 3/1987 | Volz . |
| 4,655,213 | 4/1987 | Rapoport et al. . |
| 4,660,555 | 4/1987 | Payton . |
| 4,667,669 | 5/1987 | Pasternack . |
| 4,677,975 | 7/1987 | Edgar et al. . |
| 4,686,974 | 8/1987 | Sato et al. . |
| 4,686,975 | 8/1987 | Naimon et al. . |
| 4,688,433 | 8/1987 | Sliverwater . |
| 4,766,894 | 8/1988 | Legrand et al. . |
| 4,773,411 | 9/1988 | Downs . |
| 4,776,333 | 10/1988 | Miyamae . |
| 4,790,194 | 12/1988 | Bellows et al. . |
| 4,795,314 | 1/1989 | Prybella et al. . |
| 4,796,651 | 1/1989 | Ginn et al. . |
| 4,807,616 | 2/1989 | Adahan . |
| 4,819,629 | 4/1989 | Jonson . |
| 4,823,787 | 4/1989 | Adahan . |
| 4,823,788 | 4/1989 | Smith et al. . |
| 4,827,774 | 5/1989 | Silverwater . |
| 4,827,922 | 5/1989 | Champain et al. . |
| 4,827,964 | 5/1989 | Guido et al. . |
| 4,838,257 | 6/1989 | Hatch . |
| 4,838,258 | 6/1989 | Dryden et al. . |
| 4,856,506 | 8/1989 | Jinotti . |
| 4,870,960 | 10/1989 | Hradek . |
| 4,870,963 | 10/1989 | Carter . |
| 4,877,023 | 10/1989 | Zalkin . |
| 4,879,662 | 11/1989 | Vicari et al. . |
| 4,913,401 | 4/1990 | Handke . |
| 4,915,103 | 4/1990 | Visveshwara et al. . |
| 4,934,397 | 6/1990 | Niemela et al. . |
| 4,938,210 | 7/1990 | Shene . |
| 4,938,212 | 7/1990 | Snook et al. . |
| 4,941,469 | 7/1990 | Adahan . |
| 4,944,310 | 7/1990 | Sullivan . |
| 4,957,107 | 9/1990 | Sipin . |
| 4,971,050 | 11/1990 | Bartos . |
| 4,984,601 | 1/1991 | Andersson et al. . |
| 4,986,269 | 1/1991 | Hakkinen . |
| 4,993,269 | 2/1991 | Guillaume et al. . |
| 5,002,050 | 3/1991 | McGinnis . |
| 5,009,635 | 4/1991 | Scarberry . |
| 5,024,219 | 6/1991 | Dietz . |
| 5,033,311 | 7/1991 | Custer . |
| 5,033,312 | 7/1991 | Stupecky . |
| 5,038,621 | 8/1991 | Stupecky . |
| 5,042,470 | 8/1991 | Kanesaka . |
| 5,046,491 | 9/1991 | Derrick . |
| 5,048,515 | 9/1991 | Sanso . |
| 5,063,922 | 11/1991 | Hakkinen . |
| 5,065,756 | 11/1991 | Rapoport . |
| 5,067,487 | 11/1991 | Bauman . |
| 5,081,913 | 1/1992 | Gervais . |
| 5,099,836 | 3/1992 | Rowland et al. . |
| 5,105,354 | 4/1992 | Nishimura . |
| 5,107,830 | 4/1992 | Younes . |
| 5,107,831 | 4/1992 | Halpern et al. . |
| 5,117,819 | 6/1992 | Servidio et al. . |
| 5,125,753 | 6/1992 | Ries et al. . |
| 5,129,390 | 7/1992 | Chopin et al. . |
| 5,134,890 | 8/1992 | Abrams . |
| 5,134,995 | 8/1992 | Gruenke et al. . |
| 5,137,026 | 8/1992 | Waterson et al. . |
| 5,146,941 | 9/1992 | Statler . |
| 5,148,802 | 9/1992 | Sanders et al. . |
| 5,161,525 | 11/1992 | Kimm et al. . |
| 5,165,397 | 11/1992 | Arp . |
| 5,178,138 | 1/1993 | Walstrom et al. . |
| 5,183,983 | 2/1993 | Knop . |
| 5,187,988 | 2/1993 | Dettmer et al. . |
| 5,199,424 | 4/1993 | Sullivan et al. . |
| 5,203,343 | 4/1993 | Axe et al. . |
| 5,222,478 | 6/1993 | Scarberry et al. . |
| 5,230,330 | 7/1993 | Price . |
| 5,231,979 | 8/1993 | Rose et al. . |
| 5,231,983 | 8/1993 | Matson et al. . |
| 5,234,021 | 8/1993 | Koziak et al. . |
| 5,239,995 | 8/1993 | Estes et al. . |
| 5,245,995 | 9/1993 | Sullivan et al. . |
| 5,255,687 | 10/1993 | McKenna . |
| 5,259,373 | 11/1993 | Gruenke et al. . |
| 5,271,391 | 12/1993 | Graves . |
| 5,273,031 | 12/1993 | Olsson et al. . |
| 5,280,784 | 1/1994 | Kohler . |
| 5,293,864 | 3/1994 | McFadden . |
| 5,303,738 | 4/1994 | Chang et al. . |
| 5,305,787 | 4/1994 | Thygesen . |
| 5,313,937 | 5/1994 | Zdrojkowski . |
| 5,316,261 | 5/1994 | Stoner . |
| 5,322,057 | 6/1994 | Raabe et al. . |
| 5,327,789 | 7/1994 | Nijdam . |
| 5,335,654 | 8/1994 | Rapoport . |
| 5,343,878 | 9/1994 | Scarberry et al. . |
| 5,353,788 | 10/1994 | Miles . |
| 5,363,857 | 11/1994 | Howard . |
| 5,388,571 | 2/1995 | Roberts et al. . |
| 5,398,673 | 3/1995 | Lambert . |
| 5,404,758 | 4/1995 | Huber et al. . |
| 5,404,871 | 4/1995 | Goodman et al. . |
| 5,433,193 | 7/1995 | Sanders et al. . |
| 5,443,061 | 8/1995 | Champain et al. . |
| 5,458,007 | 10/1995 | Lake . |
| 5,458,137 | 10/1995 | Axe et al. . |
| 5,479,920 | 1/1996 | Piper et al. . |
| 5,488,969 | 2/1996 | King et al. . |
| 5,490,502 | 2/1996 | Rapoport et al. . |
| 5,492,113 | 2/1996 | Estes et al. . |

| | | |
|---|---|---|
| 5,503,146 | 4/1996 | Froehlich et al. . |
| 5,507,282 | 4/1996 | Younes . |
| 5,509,404 | 4/1996 | Lloyd et al. . |
| 5,513,631 | 5/1996 | McWilliams . |
| 5,517,983 | 5/1996 | Deighan et al. . |
| 5,522,382 | 6/1996 | Sullivan et al. . |
| 5,526,805 | 6/1996 | Lutz et al. . |
| 5,532,922 | 7/1996 | Wacker et al. . |
| 5,535,738 | 7/1996 | Estes et al. . |
| 5,535,739 | 7/1996 | Rapoport et al. . |
| 5,537,997 | 7/1996 | Mechlenburg et al. . |
| 5,540,219 | 7/1996 | Mechlenburg et al. . |
| 5,540,220 | 7/1996 | Gropper . |
| 5,540,222 | 7/1996 | Younes . |
| 5,546,933 | 8/1996 | Rapoport et al. . |
| 5,546,934 | 8/1996 | Kaigler et al. . |
| 5,551,418 | 9/1996 | Estes et al. . |
| 5,551,419 | 9/1996 | Froehlich et al. . |
| 5,564,432 | 10/1996 | Thomson . |
| 5,567,127 | 10/1996 | Wentz . |
| 5,570,682 | 11/1996 | Johnson . |
| 5,598,838 | 2/1997 | Servidio et al. . |
| 5,603,315 | 2/1997 | Sasso, Jr. . |
| 5,608,647 | 3/1997 | Rubsamen et al. . |
| 5,617,846 | 4/1997 | Graetz et al. . |
| 5,632,269 | 5/1997 | Zdrojkowski . |
| 5,642,730 | 7/1997 | Baran . |
| 5,645,053 | 7/1997 | Remmers et al. . |
| 5,645,054 | 7/1997 | Cotner et al. . |
| 5,655,520 | 8/1997 | Howe et al. . |
| 5,655,522 | 8/1997 | Mechlenburg et al. . |
| 5,666,946 | 9/1997 | Langenback . |
| 5,682,878 | 11/1997 | Ogden . |
| 5,685,296 | 11/1997 | Zdrojkowski et al. . |
| 5,694,923 | 12/1997 | Hete et al. . |
| 5,701,883 | 12/1997 | Hete et al. . |
| 5,704,345 | 1/1998 | Berthon-Jones . |
| 5,709,241 | 1/1998 | Iwata ........................................ 137/527 |
| 5,715,812 | 2/1998 | Deighan et al. . |
| 5,730,121 | 3/1998 | Hawkins et al. . |
| 5,740,795 | 4/1998 | Brydon . |
| 5,752,509 | 5/1998 | Lachmann et al. . |
| 5,794,615 | 8/1998 | Estes . |
| 5,813,399 | 9/1998 | Isaza et al. . |
| 5,823,187 | 10/1998 | Estes et al. . |

FOREIGN PATENT DOCUMENTS

| | | |
|---|---|---|
| A-48748/93 | 9/1993 | Australia . |
| A-52628/93 | 7/1994 | Australia . |
| 79174/94 | 6/1995 | Australia . |
| A-34471/95 | 2/1996 | Australia . |
| A-40711/95 | 4/1996 | Australia . |
| B 34354/95 | 5/1996 | Australia . |
| A 39130/95 | 6/1996 | Australia . |
| 0 062 166 A2 | 10/1982 | European Pat. Off. . |
| 0 066 451 A1 | 12/1982 | European Pat. Off. . |
| B1 0 088 761 | 9/1983 | European Pat. Off. . |
| 93503 | 11/1983 | European Pat. Off. . |
| 0 164 500 A2 | 3/1985 | European Pat. Off. . |
| 164 500 | 12/1985 | European Pat. Off. . |
| 164-500 | 12/1985 | European Pat. Off. . |
| 0 171 321 A1 | 2/1986 | European Pat. Off. . |
| 0 185 980 | 7/1986 | European Pat. Off. . |
| 200737 B1 | 11/1986 | European Pat. Off. . |
| 0 236 850 A2 | 9/1987 | European Pat. Off. . |
| 0 872 643 A2 | 3/1988 | European Pat. Off. . |
| 274996 | 7/1988 | European Pat. Off. . |
| 298 367 A2 | 1/1989 | European Pat. Off. . |
| 347015 B1 | 12/1989 | European Pat. Off. . |
| 0 388 525 A1 | 9/1990 | European Pat. Off. . |
| 0 425 092 A1 | 5/1991 | European Pat. Off. . |
| 10 452 001 A2 | 10/1991 | European Pat. Off. . |
| 0 481 459 A1 | 4/1992 | European Pat. Off. . |
| 481 459 A1 | 4/1992 | European Pat. Off. . |
| 0549299 A2 | 6/1993 | European Pat. Off. . |
| 606 687 A2 | 7/1994 | European Pat. Off. . |
| 0705615 A1 | 9/1994 | European Pat. Off. . |
| 0 714 670 A2 | 12/1994 | European Pat. Off. . |
| 0 656 216 A2 | 6/1995 | European Pat. Off. . |
| 0 661 071 A1 | 7/1995 | European Pat. Off. . |
| 178 925 A2 | 4/1996 | European Pat. Off. . |
| 0 709 107 A1 | 5/1996 | European Pat. Off. . |
| 0 774 269 A1 | 5/1997 | European Pat. Off. . |
| 0 788 805 A2 | 8/1997 | European Pat. Off. . |
| 0811394 | 12/1997 | European Pat. Off. . |
| 0 839 545 A1 | 5/1998 | European Pat. Off. . |
| 2 596 279 | 3/1986 | France . |
| 2 574 657 A1 | 6/1986 | France . |
| 2 672 221 | 8/1992 | France . |
| 2682042 A1 | 4/1993 | France . |
| 2 733 688 | 5/1995 | France . |
| 459104 | 4/1928 | Germany . |
| 3015279 A1 | 10/1981 | Germany . |
| 34 02 603 A1 | 8/1985 | Germany . |
| 3537507 A1 | 4/1987 | Germany . |
| 3539073 A1 | 5/1987 | Germany . |
| 4432219 C1 | 4/1996 | Germany . |
| 54-104369 | 8/1979 | Japan . |
| 60-212607 | 10/1985 | Japan . |
| 62-103297 | 4/1987 | Japan . |
| 63-275352 | 11/1988 | Japan . |
| 2-173397 | 12/1988 | Japan . |
| 4-70516 | 3/1992 | Japan . |
| 06249741 | 9/1994 | Japan . |
| 6-249742 | 9/1994 | Japan . |
| 07280609 | 10/1995 | Japan . |
| 8019610 | 1/1996 | Japan . |
| 1710064 A1 | 2/1992 | Sweden . |
| 467041 | 5/1992 | Sweden . |
| 1432572 | 4/1976 | Switzerland . |
| 1432571 | 4/1976 | United Kingdom . |
| 1 444 053 | 7/1976 | United Kingdom . |
| 1 583 273 | 1/1981 | United Kingdom . |
| 2054387 | 2/1981 | United Kingdom . |
| 2 077 444 | 12/1981 | United Kingdom . |
| 2 087 570 | 5/1982 | United Kingdom . |
| 2 097 272 | 11/1982 | United Kingdom . |
| 2 147 506 | 5/1985 | United Kingdom . |
| 2 164 421 | 3/1986 | United Kingdom . |
| 2 164 569 | 3/1986 | United Kingdom . |
| 2 205 167 | 11/1988 | United Kingdom . |
| 2 223 593 | 4/1990 | United Kingdom . |
| 2 254 700 | 10/1992 | United Kingdom . |
| 2 271 811 | 4/1994 | United Kingdom . |
| 2 294 400 | 5/1996 | United Kingdom . |
| WO 80/01044 | 5/1980 | WIPO . |
| WO 82/03326 | 10/1982 | WIPO . |
| WO 82/03548 | 10/1982 | WIPO . |
| WO 86/05965 | 10/1986 | WIPO . |
| WO 86/06969 | 12/1986 | WIPO . |
| WO 88/10108 | 12/1988 | WIPO . |
| WO 89/05669 | 6/1989 | WIPO . |
| WO 89/09565 | 10/1989 | WIPO . |
| WO 89/10768 | 11/1989 | WIPO . |
| WO 90/14121 | 11/1990 | WIPO . |
| WO 92/11054 | 7/1992 | WIPO . |
| WO 92/15353 | 9/1992 | WIPO . |
| WO 92/22244 | 12/1992 | WIPO . |
| WO 93/08857 | 5/1993 | WIPO . |
| WO 93/09834 | 5/1993 | WIPO . |
| WO 93/21982 | 11/1993 | WIPO . |
| WO 93/24169 | 12/1993 | WIPO . |
| WO 94/16759 | 8/1994 | WIPO . |

| | | |
|---|---|---|
| WO 94/20051 | 9/1994 | WIPO . |
| WO 94/23780 | 10/1994 | WIPO . |
| WO 95/32016 | 11/1995 | WIPO . |
| WO 96/16688 | 6/1996 | WIPO . |
| WO 96/39216 | 12/1996 | WIPO . |
| WO 96/40336 | 12/1996 | WIPO . |
| WO 96/40337 | 12/1996 | WIPO . |
| WO 96/40338 | 12/1996 | WIPO . |
| WO 97/02064 | 1/1997 | WIPO . |
| WO 97/06844 | 2/1997 | WIPO . |
| WO 97/09090 | 3/1997 | WIPO . |
| WO 97/10019 | 3/1997 | WIPO . |
| WO 97/10868 | 3/1997 | WIPO . |
| WO 97/15343 | 5/1997 | WIPO . |
| WO 97/28838 | 8/1997 | WIPO . |
| WO 97/41812 | 11/1997 | WIPO . |
| WO 98/06449 | 2/1998 | WIPO . |
| WO 98/12965 | 4/1998 | WIPO . |
| WO 98/25662 | 6/1998 | WIPO . |
| WO 98/33433 | 8/1998 | WIPO . |
| WO 98/35715 | 8/1998 | WIPO . |
| WO 98/36245 | 8/1998 | WIPO . |
| WO 98/36338 | 8/1998 | WIPO . |
| WO 98/47554 | 10/1998 | WIPO . |
| WO 98/57691 | 12/1998 | WIPO . |

OTHER PUBLICATIONS

Nellcor Puritan Bennett; Announcing the Goodnight 314 and Goodknight 318 Nasal CPAP Systems.

Puritan Bennett; Clean, Quiet, and Comfortable . . . The Companion's 515 Nasal CPAP system; Jun. 1988.

Devilbiss Night Guard Nasal CPAP for the Treatment of Obstructive Sleep Apnea.

Sunrise; DeVilbiss Horizon LT 8001 Nasal CPAP Therapy Small in Size, big features.

DeVilbiss; Revitalizer Soft Start; The Facts Speak for Themselves.

Tranquility; Performance CPAP Advantage.

Healthdyne International; Tranquility Plus.

Respironics Inc.; Respironics' Solo CPAP System Provides Simplified OSA Therapy at an Outstanding value; Sep. 19, 1996.

Respironics Inc.; The First Family of OSA Therapy; 1991.

Fisher & Paykel Healthcare; HC200 Series Nasal CPAP Blower & Heated Humidifier.

Pierre Medical; Morphee Plus appareil de traitment des apnees du sommeil manuel d'utilisation.

Weinmann:Hamburg; Somnotron nCPAP—Great WM 2300.

Puritan Bennett; 515a Part of Our Blueprint for the Future; Mar. 1990.

Puritan Bennett; Companion 320 I/E Bi–Level Respiratory System; Apr. 1993.

ResMed; Sullivan VPAP II & II ST.

ResMed; The Sullivan V Family of CPAP Systems.

ResMed; The AutoSet Portable II.

ResMed; Sullivan Nasal CPAP System.

ResMed; The Sullivan IIID.

ResMed; The Sullivan Comfort.

DeVilbiss a Division of Sunrise Medical; Expand your Horizons With The Horizons.

Healthdyne Technologies; Home Health Care Dealer; The Journal of Home Medical Equipment and Services/Supplier; Nov. and Dec. 1997.

Healthdyne International; Tranquility Quest, The Compact CPAP for Greater patient comfort.

AirStep; Medical Products . . . Stand the Test of Time.

MAP Medical Progress for Physician und Patient; The Gentle Therapy for Sleep–Related Breathing Disorders.

Taema; Ventilation CP 90.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Fell Well, Sensitive Sleep Apnoea Therapy with Somnotron 3 and Somno–Mask System.

Respironics Inc.; Aria CPAP System.

Respironics Inc.; SleepEasy III A New Dawn in Patient Compliance.

Respironics Inc.; Multiple Choice REMstar Choice Nasal CPAP System.

MaxII nCPAP and Moritz II Bi–Level Brochure.

Derwent: Flowmeter for fluids–has turbine transducer and volumetric sensor for simultaneous calibration.

Mark Kantrowitz, Erik Horskotte and Cliff Joslyn; "Answers to Frequently Asked Questions about Fuzzy Logic and Fuzzy Expert Systems" Version 1.24 last Modified Feb. 20, 1996.

APPARATUS FOR VARYING THE FLOW AREA OF A CONDUIT

FIELD OF THE INVENTION

The present invention relates to an apparatus for varying the flow area of a conduit.

The invention has been developed primarily for use as a variable size opening for flow measurement in conjunction with upstream and downstream pressure tappings and will be described hereinafter with reference to this application.

BACKGROUND OF THE INVENTION

A known method of measuring the flow rate of a fluid (liquid or gas) through a conduit involves measuring the pressure either side of a restriction of constant area in the conduit. If the pressure drop across the restriction is recorded for a variety of known flow rates then the function of the flow rate with respect to the pressure drop can be determined. The flow rate is basically related to the pressure drop by a quadratic function (ie. the pressure drop is proportional to the square of the flow rate). When the function is known then, by measuring the pressure drop, it is possible to calculate the corresponding flow rate. Devices capable of measuring the pressure drop include, for example, electronic differential pressure transducers and fluid manometers.

Due to the quadratic relationship, small variations or errors in the measuring of the pressure drop at low flow rates produce large variations or errors in the calculated flow rate. Restrictions of constant area also produce a large pressure drop at high flow rates. Accordingly, a restriction of constant area is unsuitable when a large range of flow rates is required to be measured, especially where accuracy is required at the lower end of the range.

An example of an application where the above properties are undesirable is the flow rate measurement of air (or other breathable gas) supplied to a patient undergoing continuous positive airway pressure (CPAP) treatment for obstructive sleep apnea. In particular, when the pressure of the gas supplied to the patient is bi-level (in synchronism with patient inspiration and expiration) or autosetting in level, then accurate flow rate readings of down to zero flow are required for triggering purposes by a control system. Also, the flow rate must also be able to be measured at peak flows of up to about 200 liters per minute without a large pressure drop being caused.

A restriction of variable area can ameliorate some of the above problems. A prior art variable area restriction includes a resilient plastic flap that, in an unstressed state, almost occludes a restriction in the conduit. The flap deflects to enlarge the permitted flow area of the conduit under the influence of the fluid flowing through the restriction. The higher the air flow, the more the flap deflects, and the larger the restriction area becomes. The resilient flap can be configured to provide an almost linear relationship between pressure drop and flow rate over a useful range of flows. In this way, the resilient flap provides the desired level of accuracy at both relatively low and high flows. Further, as the area of the restriction is increased at high flows, the resilient flap does not cause a large pressure drop at these high flows.

However, the resilient flap suffers from the disadvantage that, after continuous use, it can take on a permanently deflected set and therefore provide erroneous or inaccurate readings at low flow rates.

It is an object of the present invention to substantially overcome or at least ameliorate these prior art deficiencies,

SUMMARY OF THE INVENTION

Accordingly, in a first aspect, the present invention discloses an apparatus for varying the flow area of a conduit, said apparatus including: a flap mounted in said conduit, said flap being off-centre pivotally mounted to pivot in response to flow of fluid through said conduit; and biasing means associated with said flap to rotationally urge said flap against the action of said flow.

The biasing means preferably urges said flap to a rest position when no fluid is flowing through the conduit. The flap preferably substantially occludes the conduit in the rest position. The flap is also preferably substantially perpendicular to the general direction of fluid flow through said conduit when in the rest position.

Desirably, the flap progressively pivots to progressively increase the flow area of the conduit in response to increasing fluid flow therethrough.

In a preferred embodiment, the biasing means takes the form of a magnet mounted on the flap which, in the rest position, is positioned between one or more, preferably two, magnets mounted on the conduit remote from the flap magnet. In another preferred embodiment, the flap pivots about a shaft and the biasing means includes a flap magnet eccentrically mounted on the shaft, the flap magnet, in the rest position, being positioned between at least two magnets mounted on the conduit remote the flap magnet. In one form, the shaft passes through a wall of the conduit and the flap magnet is mounted exterior the conduit. The conduit magnets are preferably symmetrically mounted either side of the flap magnet. The flap magnet and the conduit magnets are preferably adapted to provide a repelling or an attracting force therebetween to urge the flap to the rest position.

In another preferred embodiment, an attracting magnet is placed on the conduit adjacent the flap magnet, when the flap is in the rest position, to therefore attract the flap magnet and urge the flap into the rest position. In a variation of this embodiment, a ferro-magnetic metal, such as steel, is placed on the flap and is attracted by the conduit magnet to bias the flap to the rest position. Alternatively, a ferro-magnetic metal can be placed on the conduit and a flap magnet used to attract the flap into the rest position.

In a still further embodiment, a spring, for example, a clock spring, has one end attached to the flap and the other end attached to the conduit to urge the flap to the rest position.

In yet another embodiment, gravity can be used to urge the flap to the rest position. In one form of this embodiment, a weight is preferably placed on the portion of the flap below the hinge axis. In another form of this embodiment, the portion of the flap below the hinge axis is preferably configured to be larger and thereby heavier than that above. These embodiments are particularly suitable when the orientation of the apparatus is constant.

In a second aspect, the invention discloses a device for measuring flow rate as a function of differential pressure, the device including an apparatus for varying the flow area of a conduit according to the first aspect, and a means to measure the differential pressure in the conduit upstream and downstream of said flap.

BRIEF DESCRIPTION OF THE DRAWINGS

Preferred embodiments of the invention will now be described, by way of example only, with reference to the accompanying drawings in which.

DETAILED DESCRIPTION OF THE PREFERRED EMBODIMENTS

Figure 1:
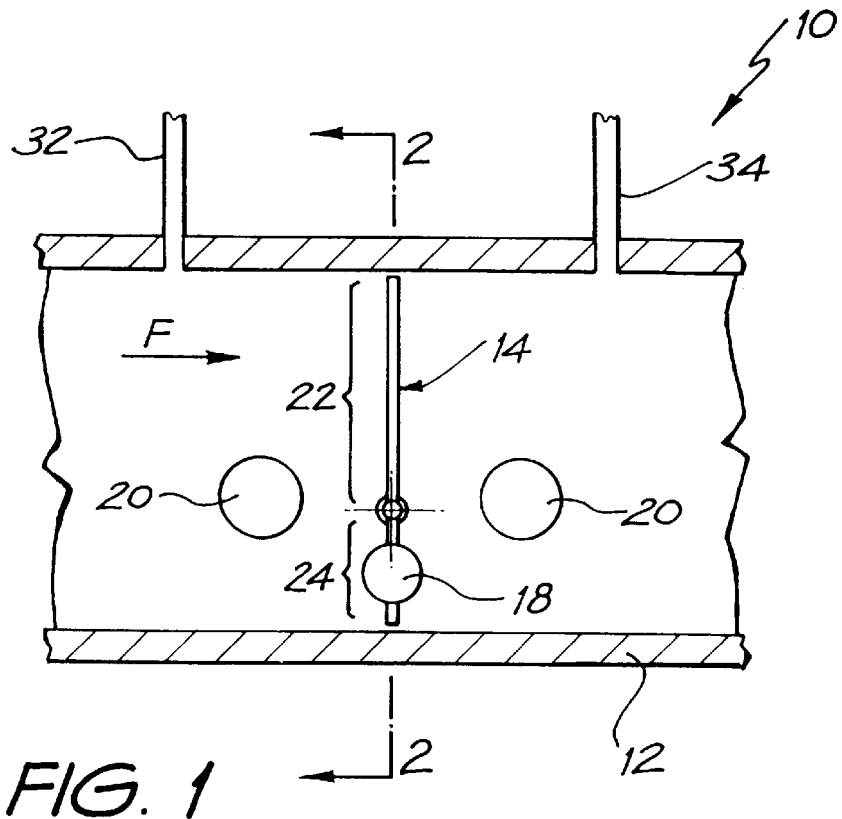
FIG. 1 is a cross-sectional side view of a first embodiment.
Figure 2:
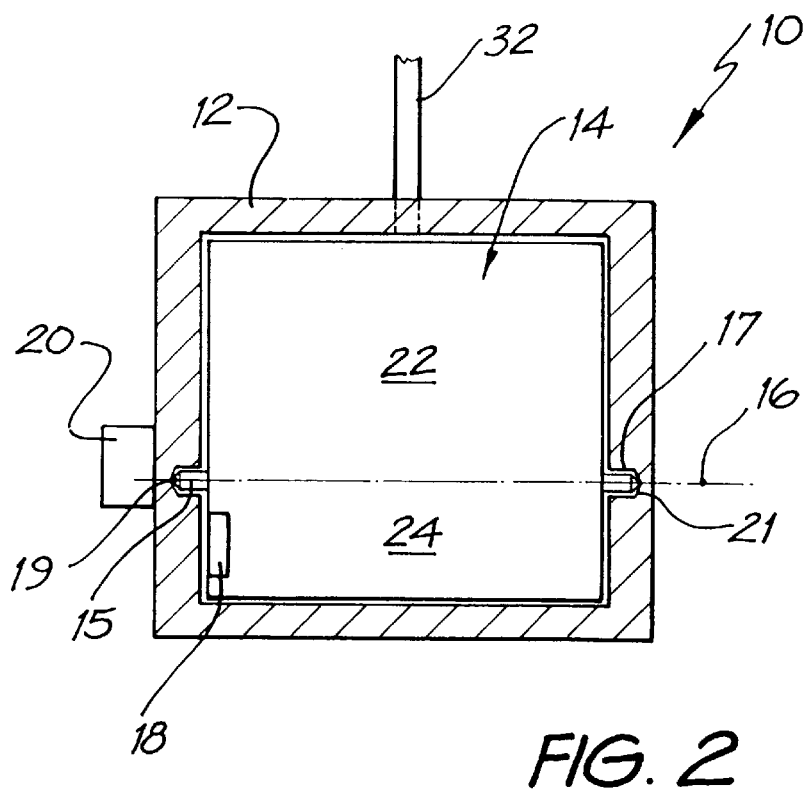
FIG. 2 is a cross-sectional end view along line 2—2 of the embodiment shown in FIG. 1.

Referring firstly to FIGS. 1 and 2, there is shown a first embodiment of an apparatus 10 for varying the flow area of a conduit 12. The apparatus takes the form of a substantially rigid flap 14 which is mounted for off-centre pivotal rotation about axis 16 in response to a flow of fluid F through the conduit 12. The flap 14 has two pivot shafts 15 that each terminate in a relatively sharp cone 19. The pivot shafts 15 are received within two pivot bores 17 which each terminate in a relatively wide cone 21 to provide point contact of low friction between each of the pivot shafts 15 and the associated pivot bores 17.

The apparatus 10 also includes biasing means in the form of flap magnet 18 and conduit magnets 20. The magnets 18 and 20 are preferably fabricated from Neodynium Iron Boron type material. The conduit magnets 20 are oriented so that they repel the flap magnet 18 and thereby urge the flap to the position shown in FIG. 1, being the position of the flap when there is no fluid flow through the conduit 12 (hereinafter referred to as the "rest" position).

The flap 14 has a relatively large region 22 and a relative small region 24 either side of the pivot axis 16. Accordingly, when fluid flow F is occurring in the conduit 12 the flap 14 is forced to pivot in the direction of arrow 26 (see FIGS. 5 and 6) about axis 16 as the force of the fluid flow F on the relatively large area 22 is higher than that on the relatively smaller area 24. The rotation of the flap 14 in the direction of arrow 26 is opposed and balanced by the repelling force between magnets 18 and 20.

Figure 3:
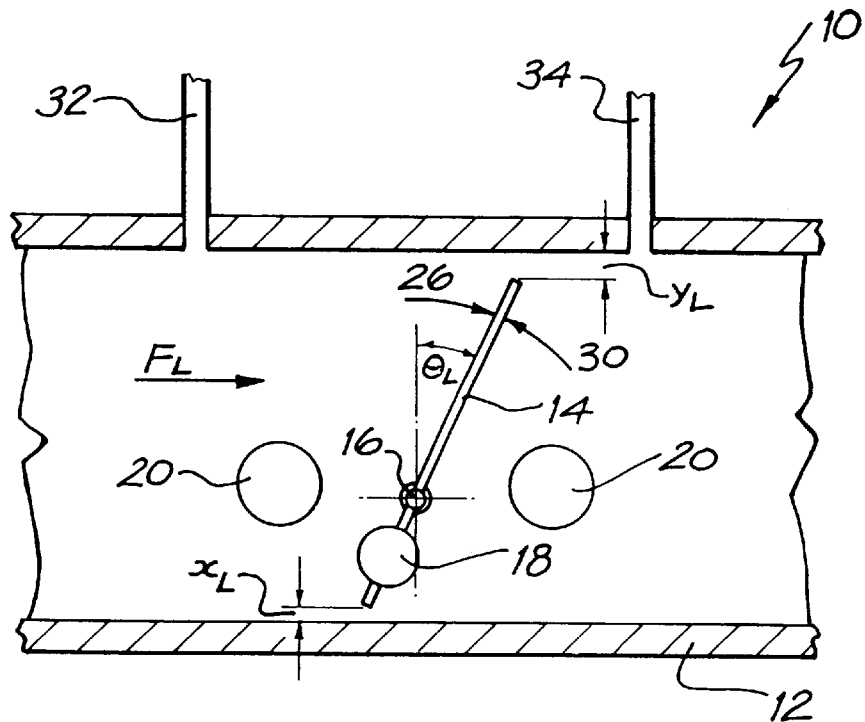
FIG. 3 is a side view of the embodiment shown in FIG. 1 under the influence of a relatively low flow rate.

FIG. 3 shows the flap 14 rotated to a position $\theta_L$ in response to the fluid flow $F_L$. In this position, the force on the flap 14 in the direction of arrow 26 is balanced by the repelling force provided by the magnets 18 and 20 in the direction of arrow 30. The flow area $A_L$ of the conduit 14 is this position is (assuming conduit width to be W) $A_L = W \times (X_L + Y_L)$.

Figure 4:
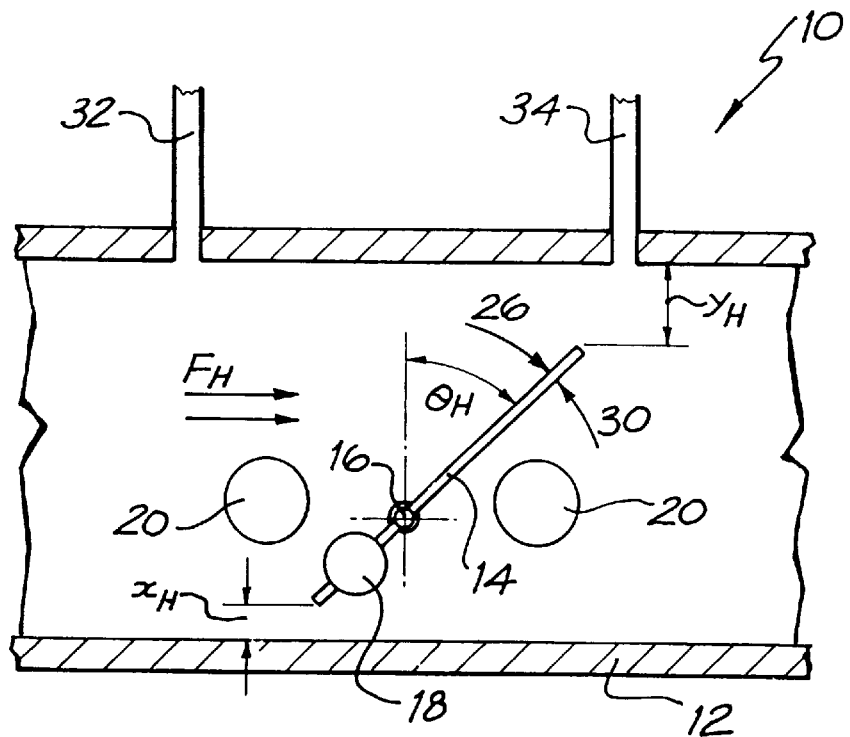
FIG. 4 is a side view of the embodiment shown in FIG. 1 under the influence of a relatively high flow rate.

FIG. 4 shows a flap under the influence of higher force $F_H$ where the flap 14 is rotated to the position $\theta_H$. In this position the flow area $A_H$ Of the conduit is $= W (X_H + Y_H)$ which is larger than $A_L$. Accordingly, the higher the flow of fluid rate F through the conduit 12 the larger the flow area of the restriction provided by the flap 14.

The apparatus 10 also includes an upstream pressure tapping 32 and a downstream pressure tapping 34. By measuring the differential pressure in the conduit 14 between the upstream and downstream pressure tappings 32 and 34, the function of the flow rate through the conduit with respect to the differential pressure can be determined. The function can be configured to be close to linear over a useful range of flows.

Figure 5:
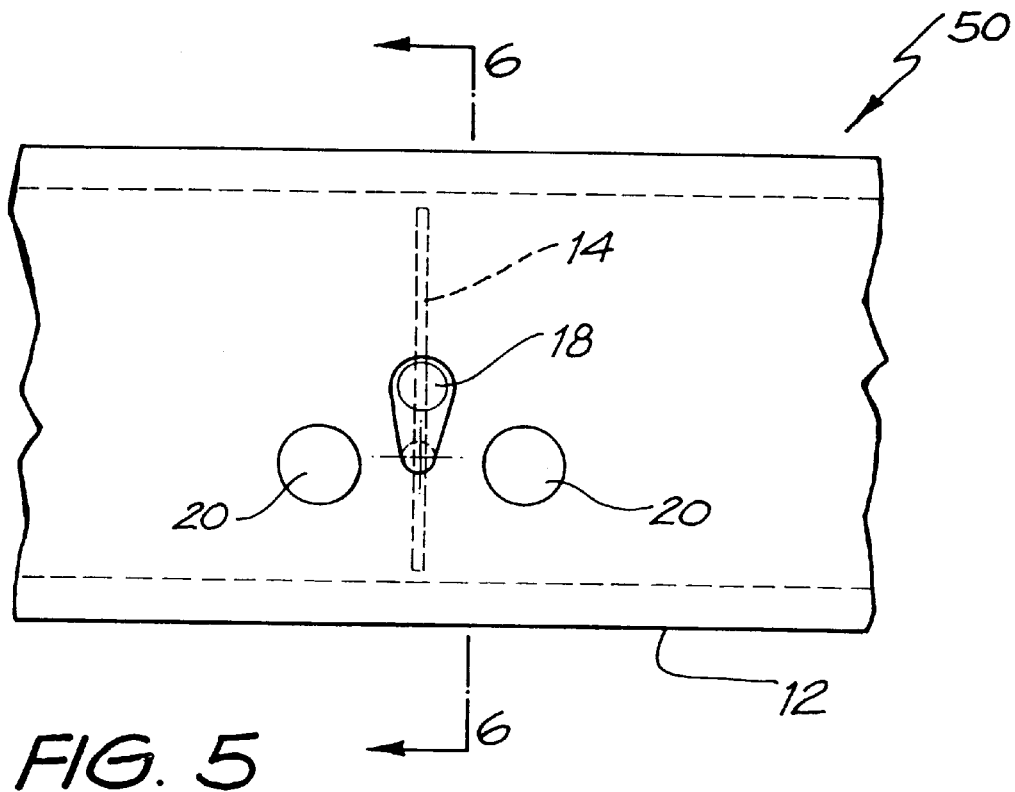
FIG. 5 is a side view of a second embodiment.
Figure 6:
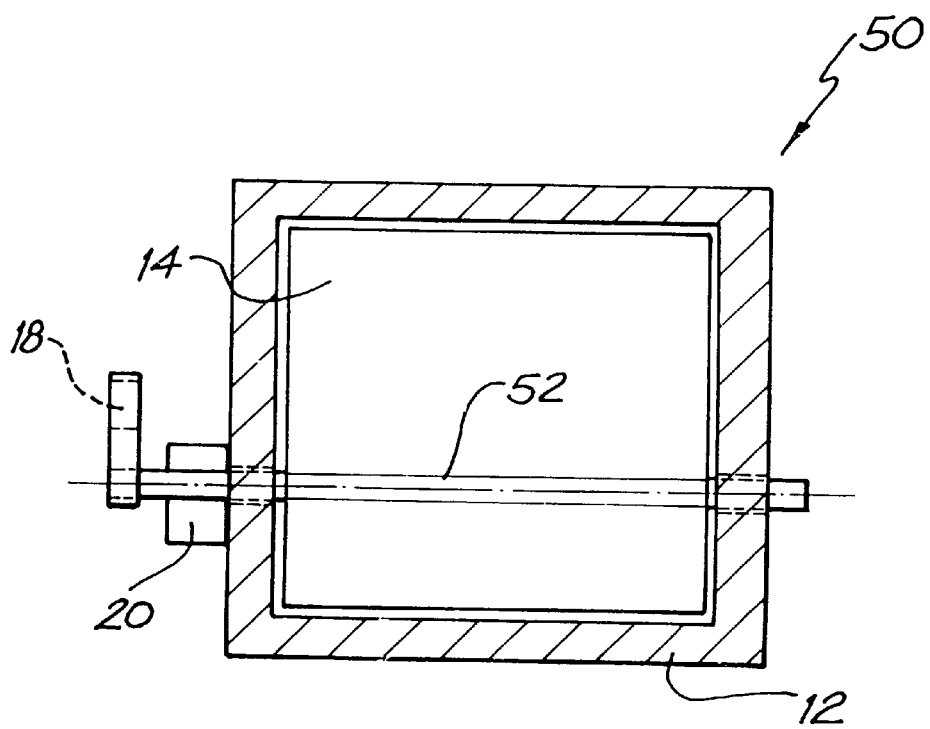
FIG. 6 is a cross sectional end view along line 8—8 of the embodiment shown in FIG. 7.

FIGS. 5 and 6 show a second embodiment of an apparatus 50 for varying the flow area of the conduit 14. The apparatus 50 has a shaft 52 which protrudes from the conduit 14. The flap magnet 18 is eccentrically mounted on the shaft 52 external the conduit 14. The conduit magnets 20 bias the flap 14 to the position shown in FIG. 7 in a similar manner to that of the first embodiment.

Figure 7:
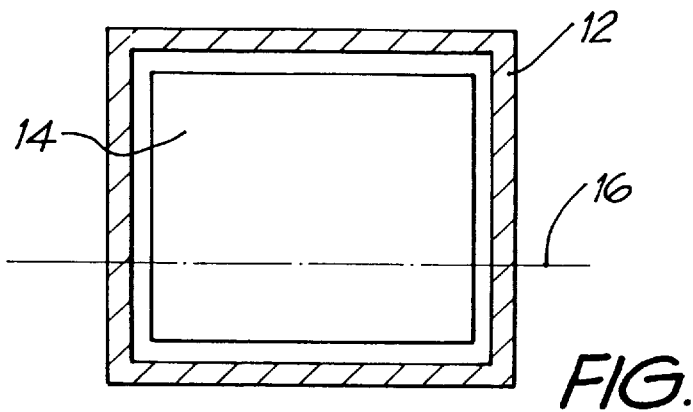
FIG. 7 is a diagranunatical end view of the embodiment shown in FIG. 1.

FIG. 7 is a diagrammatical representation of the flap 14 within the conduit 12 of the first embodiment.

Figure 8:
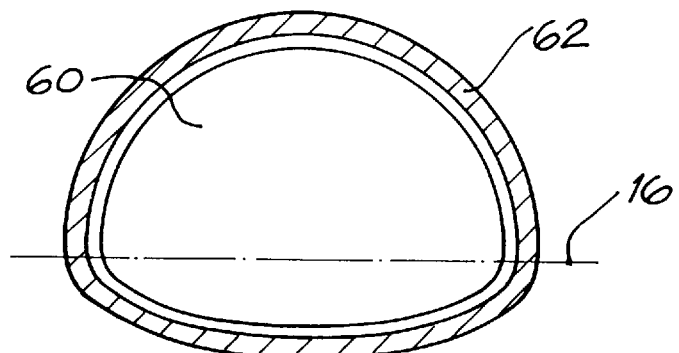
FIG. 8 is a diagrammatical end view of a third embodiment.

FIG. 8 is a diagrammatical representation of a third embodiment having an irregular shaped flap 60 provided within a correspondingly shaped conduit 62 to exemplify that the flap 60 and the conduit 62 can be of many different shapes.

Figure 9:
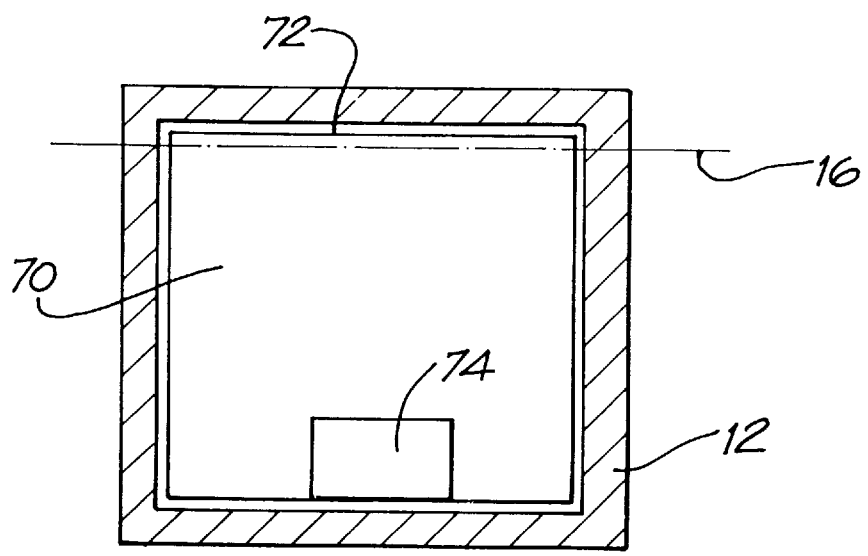
FIG. 9 is a diagrammatical end view of a fourth embodiment.

FIG. 9 is a diagrammatical representation of a fourth embodiment having a flap 70 which pivots about the axis 16 near the upper edge 72 of the flap 70 to exemplify that the off-centre pivot axis can be placed at different positions in the flap 70. Further, in this embodiment, gravity alone, or with the assistance of a weight 74, can bias the flap 70 to the rest position.

Figures 10, 11:
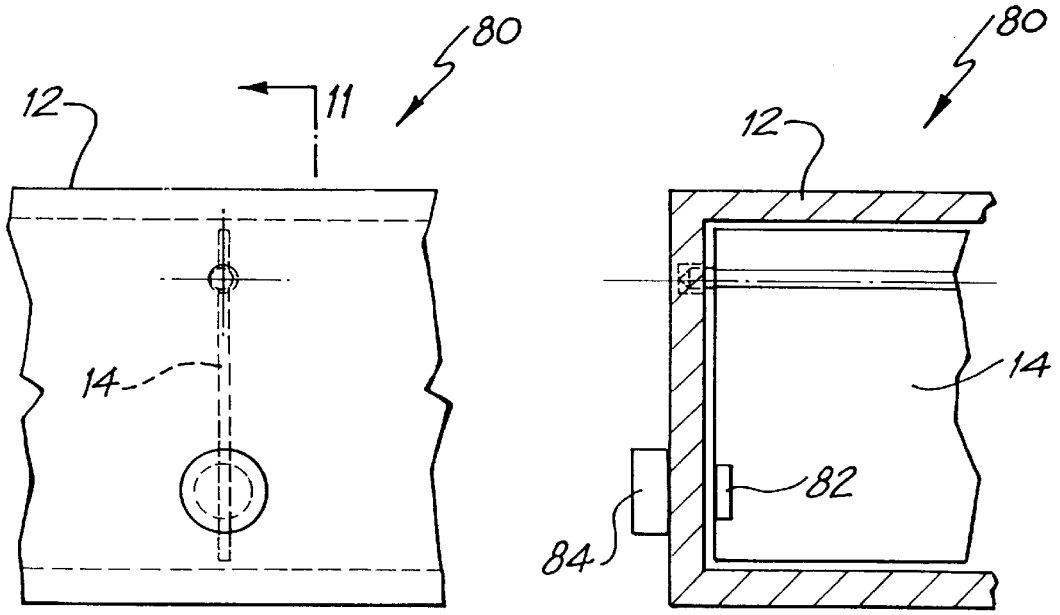
FIG. 10 is a side view of a fifth embodiment.
FIG. 11 is a cross sectional end view of the embodiment shown in FIG. 10.

FIGS. 10 and 11 show a fifth embodiment 80 in which a flap magnet 82 is used to attract a conduit magnet 84 to bias the flap 14 to the rest position shown. In a variation, one of the flap magnet or the conduit magnet can be replaced by ferromagnetic metal.

Figure 12:
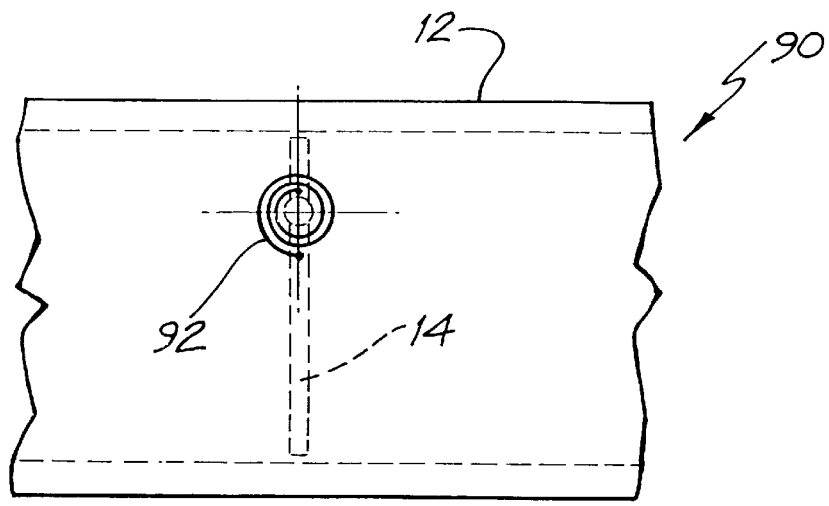
FIG. 12 is a side view of a sixth embodiment.

FIG. 12 shows a sixth embodiment 90 which uses a spring 92 to bias the flap 14 to the rest position shown. One end of the spring 92 is attached to the conduit 12 and the other to the flap 14.

In the first embodiment, the flap 14 substantially occludes the cross-sectional area of the conduit 12 in the rest position. This is a preferred configuration only and in other embodiments (not shown) the flap 14 only partially occludes the conduit when in the rest position. Similarly, in the embodiment of FIG. 1 the flap 14, in the rest position, is substantially perpendicular to the direction of fluid flow F through the conduit 12. This is also a preferred configuration and in other embodiments (not shown) the flap 14 is angled with respect to the flow direction at the rest position.

The apparatus' described above possesses the previously described advantages over the fixed area restriction as they function in the manner of a variable area restriction. Further, the apparatus' are also advantageous over the flexible flap restriction previously described as the rigid pivotable flap cannot take on a permanent deflection or set through constant use thereby increasing the accuracy of the apparatus when used for flow measurement. Also, the function between flow rate and differential pressure can be altered to provide other desired relationships by varying the flap size, shape, pivot axis or the force of the biasing means.

Although the invention has been described with reference to specific examples, it will be appreciated by those skilled in the art, that the invention can be embodied in many other forms.

I claim:

1. An apparatus for varying the flow area of a conduit, said apparatus including:

a flap mounted in said conduit, said flap being off-centre pivotally mounted to pivot in response to flow of fluid through said conduit;

a flap magnet fixedly mounted relative to the flap to pivot with the flap; and at least two conduit magnets fixedly mounted to the conduit the flap and conduit magnets adapted to rotationally urge said flap against the action of said flow.

2. An apparatus as claimed in claim 1, wherein the flap magnet and the conduit magnets urge said flap to a rest position when no fluid is flowing through the conduit.

3. An apparatus as claimed in claim 2, wherein the flap substantially occludes the conduit in the rest position.

4. An apparatus for varying the flow area of a conduit, said apparatus including:

a flap mounted in said conduit, said flap being off-centre pivotally mounted to pivot in response to flow of fluid through said conduit; and biasing means associated with said flap to rotationally urge said flap against the action of said flow, wherein the biasing means includes a magnet mounted on the flap which, in the rest position, is positioned between at least two magnets mounted on the conduit remote from the flap magnet.

5. An apparatus as claimed in claim 4, wherein the at least two conduit magnets are symmetrically mounted either side of the flap magnet.

6. An apparatus as claimed in claim 4, wherein the flap magnet and the at least two conduit magnets are adapted to provide a repelling or an attracting force therebetween to rotationally urge the flap to the rest position.

7. An apparatus for varying the flow area of a conduit, said apparatus including:

a flap mounted in said conduit, said flap being off-centre pivotally mounted to pivot in response to flow of fluid through said conduit; and biasing means associated with said flap to rotationally urge said flap against the action of said flow, wherein the biasing means urges said flap to a rest position when no fluid is flowing through the conduit, and wherein the flap pivots about a shaft and the biasing means includes a flap magnet eccentrically mounted on the shaft, the flap magnet, in the rest position, is positioned between at least two magnets mounted on the conduit remote from the flap magnet.

8. An apparatus as claimed in claim 7, wherein the shaft passes through a wall of the conduit and the flap magnet is mounted on the shaft exterior the conduit.

9. An apparatus as claimed in claim 1, wherein the flap in the rest position is substantially perpendicular to the general direction of fluid flow through said conduit.

10. An apparatus as claimed in 1, wherein the flap progressively pivots to progressively increase the flow area of the conduit in response to increasing fluid flow therethrough.

11. The apparatus of claim 1, further comprising: a means to measure the differential pressure in the conduit upstream and downstream of said flap.

12. An apparatus for varying the flow area of a conduit, said apparatus including:

a flap mounted in said conduit, said flap being off-centre pivotally mounted to pivot in response to flow of fluid through said conduit; and biasing means associated with said flap to rotationally urge said flap against the action of said flow, wherein an attracting magnet is placed on the conduit adjacent the flap magnet, when the flap is in the rest position, to attract the flap magnet and urge the flap into the rest position.

13. An apparatus for varying the flow area of a conduit, said apparatus including:

a flap mounted in said conduit, said flap being off-centre pivotally mounted to pivot in response to flow of fluid through said conduit; and biasing means associated with said flap to rotationally urge said flap against the action of said flow, wherein a ferro-magnetic metal is placed on the flap and is attracted by the conduit magnet to bias the flap to the rest position.

14. An apparatus for varying the flow area of a conduit, said apparatus including:

a flap mounted in said conduit, said flap being off-centre pivotally mounted to pivot in response to flow of fluid through said conduit; and biasing means associated with said flap to rotationally urge said flap against the action of said flow, wherein a ferro-magnetic metal can be placed on the conduit and a flap magnet used to attract the flap into the rest position.

15. An apparatus for varying the flow area of a conduit, said apparatus including:

a flap mounted in said conduit, said flap having a flap magnet mounted thereon and being off-centre pivotally mounted to pivot in response to flow of fluid through said conduit; and an attracting magnet placed on the conduit adjacent the flap magnet, the attracting magnet urging the flap to a rest position.

16. An apparatus for varying the flow area of a conduit, said apparatus including:

a flap mounted in said conduit, said flap being off-centre pivotally mounted to pivot in response to flow of fluid through said conduit, the flap being in a rest position when no fluid is flowing through the conduit;

a conduit magnet mounted on said conduit; and a ferro-magnetic metal placed on the flap adjacent the conduit magnet, the conduit magnet biasing the flap to the rest position.

17. An apparatus for varying the flow area of a conduit, said apparatus including: a flap mounted in said conduit, said flap having a flap magnet mounted thereon and being off-centre pivotally mounted to pivot in response to flow of fluid through said conduit, the flap being in a rest position when no fluid is flowing through the conduit;

a conduit magnet mounted in said conduit; and a ferro-magnetic metal placed on the conduit adjacent the flap magnet, the ferro-magnetic metal and conduit magnet attracting the flap to the rest position.

* * * * *